(12) United States Patent
Pairet et al.

(10) Patent No.: US 6,696,042 B2
(45) Date of Patent: Feb. 24, 2004

(54) PHARMACEUTICAL COMPOSITIONS BASED ON ANTICHOLINERGICS AND $NK_1$-RECEPTOR ANTAGONISTS

(75) Inventors: Michel Pairet, Stromberg (DE); Michael P. Pieper, Ingelheim (DE); Christopher J. M. Meade, Bingen (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 33 days.

(21) Appl. No.: 10/419,358

(22) Filed: Apr. 21, 2003

(65) Prior Publication Data

US 2003/0212075 A1 Nov. 13, 2003

Related U.S. Application Data

(63) Continuation of application No. 10/092,116, filed on Mar. 6, 2002.
(60) Provisional application No. 60/281,653, filed on Apr. 5, 2001.

(30) Foreign Application Priority Data

Mar. 8, 2001 (DE) .......................................... 101 11 058

(51) Int. Cl.$^7$ ........................ A61K 9/12; A61K 31/4745
(52) U.S. Cl. ........................................ 424/45; 514/291
(58) Field of Search ............................. 424/45; 514/291

(56) References Cited

U.S. PATENT DOCUMENTS

| 6,045,778 | A | * | 4/2000 | Jager et al. ..................... 424/45 |
| 6,136,824 | A | * | 10/2000 | MacLeod et al. ............ 514/317 |
| 6,455,524 | B1 | * | 9/2002 | Bozung et al. ........... 514/229.5 |
| 6,475,467 | B1 | * | 11/2002 | Keller et al. .................... 424/45 |
| 6,482,429 | B1 | * | 11/2002 | Etzler .......................... 424/440 |
| 2001/0041702 | A1 | * | 11/2001 | Crocker et al. ........... 514/236.2 |
| 2002/0137764 | A1 | * | 9/2002 | Drechsel et al. ............. 514/301 |
| 2003/0119859 | A1 | * | 6/2003 | Gavin ......................... 514/291 |

* cited by examiner

Primary Examiner—James H Reamer
(74) Attorney, Agent, or Firm—Robert P. Raymond; Mary-Ellen M. Devlin; Alan R. Stempel

(57) ABSTRACT

The present invention relates to novel pharmaceutical compositions based on anticholinergics and $NK_1$-receptor antagonists, processes for preparing them and their use in the treatment of respiratory tract diseases.

12 Claims, 3 Drawing Sheets

Figure 1:
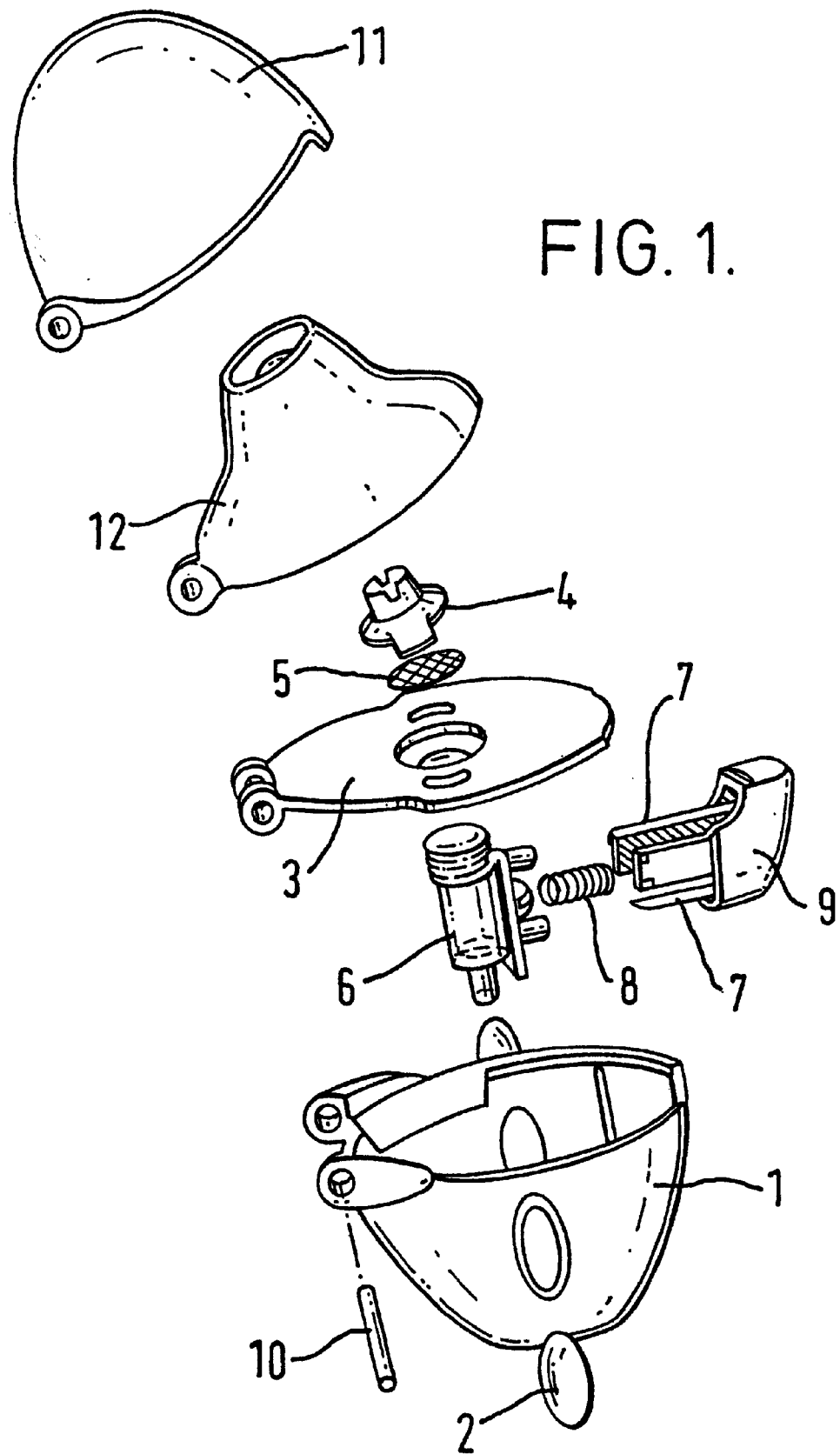

PHARMACEUTICAL COMPOSITIONS BASED ON ANTICHOLINERGICS AND NK$_1$-RECEPTOR ANTAGONISTS

This application is a continuation in part and claims the benefit of prior provisional application U.S. Serial No. 60/281,653, filed Apr. 5, 2001.

The present invention relates to novel pharmaceutical compositions based on anticholinergics and NK$_1$-receptor antagonists, processes for preparing them and their use in the treatment of respiratory diseases.

DESCRIPTION OF THE INVENTION

The present invention relates to novel pharmaceutical compositions based on anticholinergics and NK$_1$-receptor antagonists, processes for preparing them and their use in the treatment of respiratory diseases.

Surprisingly, an unexpectedly beneficial therapeutic effect, particularly a synergistic effect can be observed in the treatment of inflammatory and/or obstructive diseases of the respiratory tract if one or more, preferably one, anticholinergic is used with one or more, preferably one, NK$_1$-receptor antagonist. In view of this synergistic effect the pharmaceutical combinations according to the invention can be used in smaller doses than would be the case with the individual compounds used in monotherapy in the usual way.

The combinations of active substances according to the invention are surprisingly also characterised by a rapid onset of activity and also by a long-lasting effect. This is of great importance to the wellbeing of the patient as on the one hand he experiences a rapid improvement in his condition after the combination has been administered and also thanks to the long-lasting effect it is sufficient to take the drug once a day. The effects mentioned above may be observed both when the two active substances are administered simultaneously in a single active substance formulation and when they are administered successively in separate formulations. According to the invention, it is preferable to administer the two active substance ingredients simultaneously in a single formulation.

Within the scope of the present invention the term anticholinergics 1 denotes salts which are preferably selected from among tiotropium salts, oxitropium salts and ipratropium salts, most preferably ipratropium salts and tiotropium salts. In the above-mentioned salts the cations tiotropium, oxitropium and ipratropium are the pharmacologically active ingredients. Within the scope of the present patent application, any reference to the above cations is indicated by the use of the number 1'. Any reference to compounds 1 naturally also includes a reference to the ingredients 1' (tiotropium, oxitropium or ipratropium).

By the salts 1 which may be used within the scope of the present invention are meant the compounds which contain, in addition to tiotropium, oxitropium or ipratropium as counter-ion (anion), chloride, bromide, iodide, methanesulphonate or para-toluenesulphonate. Within the scope of the present invention, the methanesulphonate, chloride, bromide and iodide are preferred of all the salts 1, the methanesulphonate and bromide being of particular importance. Of outstanding importance according to the invention are salts 1 selected from among tiotropium bromide, oxitropium bromide and ipratropium bromide. Tiotropium bromide is particularly preferred.

Within the scope of the present invention, the word NK$_1$-receptor antagonists (hereinafter 2) denotes compounds selected from among N-[2-(3,5-bis-trifluoromethyl-phenyl)-ethyl]-2-{4-cyclopropylmethyl-piperazin-1-yl}-N-methyl-2-phenyl-acetamide (BIIF 1149), CP-122721, FK-888, NKP 608C, NKP 608A, CGP 60829, SR 48968 (Saredutant), SR 140333 (Nolpitantium besilate/chloride), LY 303 870 (Lanepitant), MEN-11420 (Nepadutant), SB 223412, MDL-105172A, MDL-103896, MEN-11149, MEN-11467, DNK 333A, SR-144190, YM-49244, YM-44778, ZM-274773, MEN-10930, S-19752, Neuronorm, YM-35375, DA-5018, Aprepitant (MK-869), L-754030, CJ-11974, L-758298, DNK-33A, 6b-I, CJ-11974, TAK-637, GR 205171 and the arylglycinamide derivatives of general formula 3

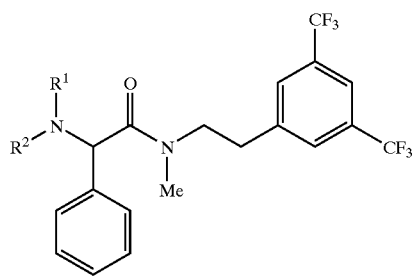

3 wherein
R$^1$ and R$^2$ together with the N to which they are bound form a ring of formula

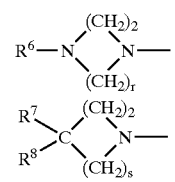

wherein r and s are 2 or 3;
R$^6$ denotes H, —C$_1$–C$_5$-alkyl, C$_3$–C$_5$-alkenyl, propynyl, hydroxy(C$_2$–C$_4$)alkyl, methoxy(C$_2$–C$_4$) alkyl, di(C$_1$–C$_3$)alkylamino(C$_2$–C$_4$)alkyl, amino (C$_2$–C$_4$)alkyl, amino, di(C$_1$–C$_3$)alkylamino, monofluoro to perfluoro(C$_1$–C$_2$)alkyl, N-methylpiperidinyl, pyridyl, pyrimidinyl, pyrazinyl or pyridazinyl,
R$^7$ has one of the meanings (a) to (d),
(a) hydroxy
(b) 4-piperidinopiperidyl,
(c)

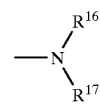

wherein R$^{16}$ and R$^{17}$ independently of each other denote H, (C$_1$–C$_4$)alkyl, (C$_3$–C$_6$)cycloalkyl, hydroxy (C$_2$–C$_4$)alkyl, dihydroxy(C$_2$–C$_4$)alkyl, (C$_1$–C$_3$) alkoxy(C$_2$–C$_4$)alkyl, phenyl(C$_1$–C$_4$)alkyl or di(C$_1$–C$_3$)alkylamino(C$_2$–C$_4$)alkyl,
R$^8$ denotes H,
optionally in the form of the enantiomers and mixtures of enantiomers thereof, optionally in the form of the racemates thereof.

The abovementioned compounds of formula 3 are known for example from International Patent Applications WO 96/32386 and WO 97/32865, to which reference is hereby made in their entirety.

Preferably, the compound 2 is selected from among BIIF 1149, CP-122721, CGP 60829, MK-869, CJ-11974, GR 205171 and the arylglycinamide derivatives of general formula 3, wherein $R^1$ and $R^2$ together with the N to which they are bound form a ring of formula

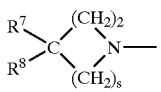

wherein s is 2 or 3;
$R^7$ denotes a group

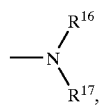

wherein $R^{16}$ and $R^{17}$ independently of each other denote H, $(C_1-C_4)$alkyl, $(C_3-C_6)$cycloalkyl, hydroxy$(C_2-C_4)$alkyl, dihydroxy$(C_2-C_4)$alkyl, $(C_1-C_3)$alkoxy$(C_2-C_4)$alkyl, phenyl$(C_1-C_4)$alkyl or di$(C_1-C_3)$alkylamino$(C_2-C_4)$alkyl, $R^8$ denotes H, optionally in the form of the enantiomers and mixtures of enantiomers thereof and optionally in the form of the racemates thereof.

Particularly preferably, the compound 2 is selected from among BIIF1149 and the arylglycinamide derivatives of general formula 3, wherein $R^1$ and $R^2$ together with the N to which they are bound form a ring of formula

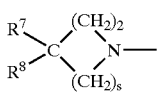

wherein s is 2 and
$R^7$ denotes a group

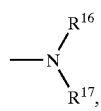

wherein $R^{16}$ and $R^{17}$ independently of each other denote H, $(C_1-C_4)$alkyl, $(C_3-C_6)$cycloalkyl, hydroxy$(C_2-C_4)$alkyl or dihydroxy$(C_2-C_4)$alkyl, $R^8$ denotes H, optionally in the form of the enantiomers and mixtures of enantiomers thereof and optionally in the form of the racemates thereof.

Most particularly preferred as compounds of formula 2 are N-[2-(3,5-bis-trifluoromethyl-phenyl)-ethyl]-2-{4-[(3-hydroxy-propyl)-methyl-amino]-piperidin-1-yl}-N-methyl-2-phenyl-acetamide, N-[2-(3,5-bis-trifluoromethyl-phenyl)-ethyl]-2-[4-(2-hydroxy-1-hydroxymethyl-ethylamino)-piperidin-1-yl]-N-methyl-2-phenylacetamide, N-[2-(3,5-bis-trifluoromethyl-phenyl)-ethyl]-2-[4-(cyclopropylmethyl-methyl-amino)-piperidin-1-yl]-N-methyl-2-phenyl-acetamide, N-[2-(3,5-bis-trifluoromethyl-phenyl)-ethyl]-2-{4-[(2-hydroxy-ethyl)-(3-hydroxy-propyl)-amino]-piperidin-1-yl}-N-methyl-2-phenyl-acetamide and N-[2-(3,5-bis-trifluoromethyl-phenyl)-ethyl]-2-{4-[cyclopropylmethyl-(3-hydroxy-propyl)-amino]-piperidin-1-yl}-N-methyl-2-phenyl-acetamide, optionally in the form of the enantiomers and mixtures of enantiomers thereof and optionally in the form of the racemates thereof.

Of particular importance is N-[2-(3,5-bis-trifluoromethyl-phenyl)-ethyl]-2-[4-(2-hydroxy-1-hydroxymethyl-ethylamino)-piperidin-1-yl]-N-methyl-2-phenylacetamide, optionally in the form of its enantiomers, preferably in the form of its (S)-enantiomer, optionally in the form of the mixtures of enantiomers thereof, and optionally in the form of the racemates thereof.

Examples of alkyl groups (including those which are part of other groups), unless otherwise defined, are branched and unbranched alkyl groups with 1 to 5 carbon atoms, such as, for example: methyl, ethyl, propyl, 1-methylethyl (isopropyl), n-butyl, 1-methylpropyl, 2-methylpropyl, 1,1-dimethylethyl(tert.butyl), etc. The definitions propyl, butyl and pentyl always include the associated isomeric groups. Hydroxy or dihydroxyalkyl groups are alkyl groups substituted by one or two hydroxy groups.

Examples of alkenyl groups (including those which are part of other groups) are branched and unbranched alkenyl groups with 3 to 5 carbon atoms, provided that they have at least one double bond, such as, for example, propenyl, isopropenyl, butenyl, etc.

Cycloalkyl generally denotes a saturated cyclic hydrocarbon group having 3 to 6 carbon atoms. Examples include cyclopropyl, cyclobutyl, cyclopentyl, cyclohexyl, cyclopropylmethyl, cyclobutylmethyl, cyclopentylmethyl, cyclopropylethyl, cyclobutylethyl, etc.

Alkyloxy, which may optionally also be referred to as alkoxy, denotes a straight-chain or branched alkyl group bound via an oxygen atom. The methoxy group is particularly preferred.

Any reference to the abovementioned $NK_1$-receptor antagonists 2 within the scope of the present invention includes a reference to any pharmacologically acceptable acid addition salts thereof which may exist.

By the physiologically acceptable acid addition salts which may be formed from 2 are meant, for example, pharmaceutically acceptable salts selected from the salts of hydrochloric acid, hydrobromic acid, sulphuric acid, phosphoric acid, methanesulphonic acid, acetic acid, fumaric acid, succinic acid, lactic acid, citric acid, tartaric acid or maleic acid. Particularly preferred salts of the compounds 2 according to the invention are those selected from among the acetate, hydrochloride, hydrobromide, sulphate, phosphate and methanesulphonate.

The pharmaceutical combinations of 1 and 2 according to the invention are preferably administered by inhalation. Suitable inhalable powders packed into suitable capsules (inhalettes) may be administered using suitable powder inhalers. Alternatively, the drug may be inhaled by the application of suitable inhalation aerosols. These also include powdered inhalation aerosols which contain for example HFA134a, HFA227 or a mixture thereof as propellant gas. The drug may also be inhaled using suitable solutions of the pharmaceutical combination consisting of 1 and 2.

In one aspect, therefore, the invention relates to a pharmaceutical composition which contains a combination of 1 and 2.

In another aspect the present invention relates to a pharmaceutical composition which contains one or more salts 1 and one or more compounds 2, optionally in the form of their solvates or hydrates. Again, the active substances may be combined in a single preparation or contained in two separate formulations. Pharmaceutical compositions which contain the active substances 1 and 2 in a single preparation are preferred according to the invention.

In another aspect the present invention relates to a pharmaceutical composition which contains, in addition to therapeutically effective quantities of 1 and 2, a pharmaceutically acceptable carrier or excipient. In another aspect the present invention relates to a pharmaceutical composition which does not contain any pharmaceutically acceptable carrier or excipient in addition to therapeutically effective quantities of 1 and 2.

The present invention also relates to the use of 1 and 2 for preparing a pharmaceutical composition containing therapeutically effective quantities of 1 and 2 for treating inflammatory and/or obstructive diseases of the respiratory tract, particularly asthma or chronic obstructive pulmonary disease (COPD), and complications thereof such as pulmonary hypertension, as well as allergic and non-allergic rhinitis, provided that treatment with $NK_1$-receptor antagonists is not contraindicated from a therapeutic point of view, by simultaneous or successive administration.

The present invention also relates to the simultaneous or successive use of therapeutically effective doses of the combination of the above pharmaceutical compositions 1 and 2 for treating inflammatory and/or obstructive diseases of the respiratory tract, particularly asthma or chronic obstructive pulmonary disease (COPD), and complications thereof such as pulmonary hypertension, as well as allergic and non-allergic rhinitis, provided that treatment with $NK_1$-receptor antagonists is not contraindicated from a therapeutic point of view, by simultaneous or successive administration.

In the active substance combinations of 1 and 2 according to the invention, ingredients 1 and 2 may be present in the form of their enantiomers, mixtures of enantiomers or in the form of racemates.

The proportions in which the two active substances 1 and 2 may be used in the active substance combinations according to the invention are variable. Active substances 1 and 2 may possibly be present in the form of their solvates or hydrates. Depending on the choice of the compounds 1 and 2, the weight ratios which may be used within the scope of the present invention vary on the basis of the different molecular weights of the various compounds and their different potencies. As a rule, the pharmaceutical combinations according to the invention may contain compounds 1 and 2 in ratios by weight ranging from 1:300 to 50:1, preferably from 1:250 to 40:1. In the particularly preferred pharmaceutical combinations which contain tiotropium salt as compound 1 and a compound selected from among BIIF 1149, CGP 60829, MK-869, CJ-11974, GR 205171, N-[2-(3,5-bis-trifluoromethyl-phenyl)-ethyl]-2-{4-[(3-hydroxy-propyl)-methyl-amino]-piperidin-1-yl}-N-methyl-2-phenyl-acetamide, N-[2-(3,5-bis-trifluoromethyl-phenyl)-ethyl]-2-[4-(2-hydroxy-1-hydroxymethyl-ethylamino)-piperidin-1-yl]-N-methyl-2-phenylacetamide, N-[2-(3,5-bis-trifluoromethyl-phenyl)-ethyl]-2-[4-(cyclopropylmethyl-methyl-amino)-piperidin-1-yl]-N-methyl-2-phenyl-acetamide, N-[2-(3,5-bis-trifluoromethyl-phenyl)-ethyl]-2-{4-[(2-hydroxy-ethyl)-(3-hydroxy-propyl)-amino]-piperidin-1-yl}-N-methyl-2-phenyl-acetamide and N-[2-(3,5-bis-trifluoromethyl-phenyl)-ethyl]-2-{4-[cyclopropylmethyl-(3-hydroxy-propyl)-amino]-piperidin-1-yl}-N-methyl-2-phenyl-acetamide and the arylglycinamide derivatives of formula 3 as $NK_1$-receptor antagonist 2, the weight ratios of 1 to 2 are most preferably in a range in which tiotropium 1' and 2 are present in proportions of 1:150 to 30:1, more preferably from 1:50 to 20:1.

For example, without restricting the scope of the invention thereto, preferred combinations of 1 and 2 according to the invention may contain tiotropium 1' and $NK_1$-receptor antagonist 2 in the following weight ratios:

1:80, 1:79, 1:78, 1:77, 1:76, 1:75, 1:74, 1:73, 1:72, 1:71, 1:70, 1:69, 1:68, 1:67, 1:66, 1:65, 1:64, 1:63, 1:62, 1:61, 1:60, 1:59, 1:58, 1:57, 1:56, 1:55, 1:54, 1:53, 1:52, 1:51, 1:50; 1:49; 1:48; 1:47; 1:46; 1:45; 1:44; 1:43; 1:42; 1:41; 1:40; 1:39; 1:38; 1:37; 1:36; 1:35; 1:34; 1:33; 1:32; 1:31; 1:30; 1:29; 1:28; 1:27; 1:26; 1:25; 1:24; 1:23; 1:22; 1:21; 1:20; 1:19; 1:18; 1:17; 1:16; 1:15; 1:14; 1:13; 1:12; 1:11; 1:10; 1:9; 1:8; 1:7; 1:6; 1:5; 1:4; 1:3; 1:2; 1:1; 2:1; 3:1; 4:1; 5:1; 6:1; 7:1; 8:1; 9:1; 10:1; 11:1; 12:1; 13:1; 14:1; 15:1; 16:1; 17:1; 18:1; 19:1; 20:1.

The pharmaceutical compositions according to the invention containing the combinations of 1 and 2 are normally administered so that 1 and 2 are present together in doses of 0.01 to 10000 μg, preferably from 0.1 to 2000 μg, more preferably from 1 to 1500 μg, better still from 50 to 1200 μg per single dose. For example, combinations of 1 and 2 according to the invention contain a quantity of tiotropium 1' and $NK_1$-receptor antagonist 2 such that the total dosage per single dose is about 100 μg, 105 μg, 110 μg, 115 μg, 120 μg, 125 μg, 130 μg, 135 μg, 140 μg, 145 μg, 150 μg, 155 μg, 160 μg, 165 μg, 170 μg, 175 μg, 180 μg, 185 μg, 190 μg, 195 μg, 200 μg, 205 μg, 210 μg, 215 μg, 220 μg, 225 μg, 230 μg, 235 μg, 240 μg, 245 μg, 250 μg, 255 μg, 260 μg, 265 μg, 270 μg, 275 μg, 280 μg, 285 μg, 290 μg, 295 μg, 300 μg, 305 μg, 310 μg, 315 μg, 320 μg, 325 μg, 330 μg, 335 μg, 340 μg, 345 μg, 350 μg, 355 μg, 360 μg, 365 μg, 370 μg, 375 μg, 380 μg, 385 μg, 390 μg, 395 μg, 400 μg, 405 μg, 410 μg, 415 μg, 420 μg, 425 μg, 430 μg, 435 μg, 440 μg, 445 μg, 450 μg, 455 μg, 460 μg, 465 μg, 470 μg, 475 μg, 480 μg, 485 μg, 490 μg, 495 μg, 500 μg, 505 μg, 510 μg, 515 μg, 520 μg, 525 μg, 530 μg, 535 μg, 540 μg, 545 μg, 550 μg, 555 μg, 560 μg, 565 μg, 570 μg, 575 μg, 580 μg, 585 μg, 590 μg, 595 μg, 600 μg, 605 μg, 610 μg, 615 μg, 620 μg, 625 μg, 630 μg, 635 μg, 640 μg, 645 μg, 650 μg, 655 μg, 660 μg, 665 μg, 670 μg, 675 μg, 680 μg, 685 μg, 690 μg, 695 μg, 700 μg, 705 μg, 710 μg, 715 μg, 720 μg, 725 μg, 730 μg, 735 μg, 740 μg, 745 μg, 750 μg, 755 μg, 760 μg, 765 μg, 770 μg, 775 μg, 780 μg, 785 μg, 790 μg, 795 μg, 800 μg, 805 μg, 810 μg, 815 μg, 820 μg, 825 μg, 830 μg, 835 μg, 840 μg, 845 μg, 850 μg, 855 μg, 860 μg, 865 μg, 870 μg, 875 μg, 880 μg, 885 μg, 890 μg, 895 μg, 900 μg, 905 μg, 910 μg, 915 μg, 920 μg, 925 μg, 930 μg, 935 μg, 940 μg, 945 μg, 950 μg, 955 μg, 960 μg, 965 μg, 970 μg, 975 μg, 980 μg, 985 μg, 990 μg, 995 μg, 1000 μg, 1005 μg, 1010 μg, 1015 μg, 1020 μg, 1025 μg, 1030 μg, 1035 μg, 1040 μg, 1045 μg, 1050 μg, 1055 μg, 1060 μg, 1065 μg, 1070 μg, 1075 μg, 1080 μg, 1085 μg, 1090 μg, 1095 μg, 1100 μg or similar. The suggested dosages per single dose specified above are not to be regarded as being limited to the numerical values actually stated, but are intended as dosages which are disclosed by way of example. Of course, dosages which may fluctuate about the abovementioned numerical values within a range of about +/-2.5 μg are also included in the values given above by way of example. In these dosage ranges, the active substances 1' and 2 may be present in the weight ratios given above.

For example, without restricting the scope of the invention thereto, the combinations of 1 and 2 according to the invention may contain a quantity of tiotropium 1' and NK$_1$-receptor antagonist 2 such that, for each single dose, 5 μg of 1' and 25 μg of 2, 5 μg of 1' and 50 μg of 2, 5 μg of 1' and 100 μg of 2, 5 μg of 1' and 200 μg of 2, 5 μg of 1' and 300 μg of 2, 5 μg of 1' and 400 μg of 2, 5 μg of 1' and 500 μg of 2, 5 μg of 1' and 600 μg of 2, 5 μg of 1' and 700 μg of 2, 5 μg of 1' and 800 μg of 2, 5 μg of 1' and 900 μg of 2, 5 μg of 1' and 1000 μg of 2, 10 μg of 1' and 25 μg of 2, 10 μg of 1' and 50 μg of 2, 10 μg of 1' and 100 μg of 2, 10 μg of 1' and 200 μg of 2, 10 μg of 1' and 300 μg of 2, 10 μg of 1' and 400 μg of 2, 10 μg of 1' and 500 μg of 2, 10 μg of 1' and 600 μg of 2, 10 μg of 1' and 700 μg of 1, 10 μg of 1' and 800 μg of 2, 10 μg of 1' and 900 μg of 2, 10 μg of 1' and 1000 μg of 2, 18 μg of 1' and 25 μg of 2, 18 μg of 1' and 50 μg of 2, 18 μg of 1' and 100 μg of 2, 18 μg of 1' and 200 μg of 2, 18 μg of 1' and 300 μg of 2, 18 μg of 1' and 400 μg of 2, 18 μg of 1' and 500 μg of 2, 18 μg of 1' and 600 μg of 2, 18 μg of 1' and 700 μg of 2, 18 μg of 1' and 800 μg of 2, 18 μg of 1' and 900 μg of 2, 18 μg of 1' and 1000 μg of 2, 20 μg of 1' and 25 μg of 2, 20 μg of 1' and 50 μg of 2, 20 μg of 1' and 50 μg of 2, 20 μg of 1' and 100 μg of 2, 20 μg of 1' and 200 μg of 2, 2 μg of 1' and 300 μg of 2, 20 μg of 1' and 400 μg of 2, 20 μg of 1' and 500 μg of 2, 20 μg of 1' and 600 μg of 2, 20 μg of 1' and 700 μg of 2, 20 μg of 1' and 800 μg of 2, 20 μg of 1' and 900 μg of 2, 20 μg of 1' and 1000 μg of 2, 36 μg of 1' and 25 μg of 2, 36 μg of 1' and 50 μg of 2, 36 μg of 1' and 100 μg of 1, 36 μg of 1' and 200 μg of 2, 36 μg of 1' and 300 μg of 2, 36 μg of 1' and 400 μg of 2, 36 μg of 1' and 500 μg of 2, 36 μg of 1' and 600 μg of 2, 36 μg of 1' and 700 μg of 2, 36 μg of 1' and 800 μg of 2, 36 μg of 1' and 900 μg of 2, 36 μg of 1' and 1000 μg of 2, 40 μg of 1' and 25 μg of 2, 40 μg of 1' and 50 μg of 2, 40 μg of 1' and 100 μg of 2, 40 μg of 1' and 200 μg of 2, 40 μg of 1' and 300 μg of 2, 40 μg of 1' and 400 μg of 2, 40 μg of 1' and 500 μg of 2, 40 μg of 1' and 600 μg of 2, or 40 μg of 1' and 700 μg of 2, 40 μg of 1' and 800 μg of 2, 40 μg of 1' and 900 μg of 2, 40 μg of 1' and 1000 μg of 2, are administered.

If the active substance combination in which 1 denotes tiotropium bromide is used as the preferred combination of 1 and 2 according to the invention, the quantities of active substance 1' and 2 administered per single dose mentioned by way of example correspond to the following quantities of 1 and 2 administered per single dose: 6 μg of 1 and 25 μg of 2, 6 μg of 1 and 50 μg of 2, 6 μg of 1 and 100 μg of 2, 6 μg of 1 and 200 μg of 2, 6 μg of 1 and 300 μg of 2, 6 μg of 1 and 400 μg of 2, 6 μg of 1 and 500 μg of 2, 6 μg of 1 and 600 μg of 2, 6 μg of 1 and 700 μg of 2, 6 μg of 1 and 800 μg of 2, 6 μg of 1 and 900 μg of 2, 6 μg of 1 and 1000 μg of 2, 12 μg of 1 and 25 μg of 2, 12 μg of 1 and 50 μg of 2, 12 μg of 1 and 100 μg of 2, 12 μg of 1 and 200 μg of 2, 12 μg of 1 and 300 μg of 2, 12 μg of 1 and 400 μg of 2, 12 μg of 1 and 500 μg of 2, 12 μg of 1 and 600 μg of 2, 12 μg of 1 and 700 μg of 2, 12 μg of 1 and 800 μg of 2, 12 μg of 1 and 900 μg of 2, 12 μg of 1 and 1000 μg of 2, 21.7 μg of 1 and 25 μg of 2, 21.7 μg of 1 and 50 μg of 2, 21.7 μg of 1 and 100 μg of 2, 21.7 μg of 1 and 200 μg of 2, 21.7 μg of 1 and 300 μg of 2, 21.7 μg of 1 and 400 μg of 2, 21.7 μg of 1 and 500 μg of 2, 21.7 μg of 1 and 600 μg of 2, 21.7 μg of 1 and 700 μg of 2, 21.7 μg of 1 and 800 μg of 2, 21.7 μg of 1 and 900 μg of 2, 21.7 μg of 1 and 1000 μg of 2, 24.1 μg of 1 and 25 μg of 2, 24.1 μg of 1 and 50 μg of 2, 24.1 μg of 1 and 100 μg of 2, 24.1 μg of 1 and 200 μg of 2, 24.1 μg of 1 and 300 μg of 2, 24.1 μg of 1 and 400 μg of 2, 24.1 μg of 1 and 500 μg of 2, 24.1 μg of 1 and 600 μg of 2, 24.1 μg of 1 and 700 μg of 2, 24.1 μg of 1 and 800 μg of 2, 24.1 μg of 1 and 900 μg of 2, 24.1 μg of 1 and 1000 μg of 2, 43.3 μg of 1 and 25 μg of 2, 43.3 μg of 1 and 50 μg of 2, 43.3 μg of 1 and 100 μg of 2, 43.3 μg of 1 and 200 μg of 2, 43.3 μg of 1 and 300 μg of 2, 43.3 μg of 1 and 400 μg of 2, 43.3 μg of 1 and 500 μg of 2, 43.3 μg of 1 and 600 μg of 2, 43.3 μg of 1 and 700 μg of 2, 43.3 μg of 1 and 800 μg of 2, 43.3 μg of 1 and 900 μg of 2, 43.3 μg of 1 and 1000 μg of 2, 48.1 μg of 1 and 25 μg of 2, 48.1 μg of 1 and 50 μg of 2, 48.1 μg of 1 and 100 μg of 2, 48.1 μg of 1 and 200 μg of 2, 48.1 μg of 1 and 300 μg of 2, 48.1 μg of 1 and 400 μg of 2, 48.1 μg of 1 and 500 μg of 2, 48.1 μg of 1 and 600 μg of 2, 48.1 μg of 1 and 700 μg of 2, 48.1 μg of 1 and 800 μg of 2, 48.1 μg of 1 and 900 μg of 2, 48.1 μg of 1 and 1000 μg of 2.

If the active substance combination in which 1 is tiotropium bromide monohydrate is used as the preferred combination of 1 and 2 according to the invention, the quantities of 1' and 2 administered per single dose specified by way of example hereinbefore correspond to the following quantities of 1 and 2 administered per single dose: 6.2 μg of 1 and 25 μg of 2, 6.2 μg of 1 and 50 μg of 2, 6.2 μg of 1 and 100 μg of 2, 6.2 μg of 1 and 200 μg of 2, 6.2 μg of 1 and 300 μg of 2, 6.2 μg of 1 and 400 μg of 2, 6.2 μg of 1 and 500 μg of 2, 6.2 μg of 1 and 600 μg of 2, 6.2 μg of 1 and 700 μg of 2, 6.2 μg of 1 and 800 μg of 2, 6.2 μg of 1 and 900 μg of 2, 6.2 μg of 1 and 1000 μg of 2, 12.5 μg of 1 and 25 μg of 2, 12.5 μg of 1 and 50 μg of 2, 12.5 μg of 1 and 100 μg of 2, 12.5 μg of 1 and 200 μg of 2, 12.5 μg of 1 and 300 μg of 2, 12.5 μg of 1 and 400 μg of 2, 12.5 μg of 1 and 500 μg of 2, 12.5 μg of 1 and 600 μg of 2, 12.5 μg of 1 and 700 μg of 2, 12.5 μg of 1 and 800 μg of 2, 12.5 μg of 1 and 900 μg of 2, 12.5 μg of 1 and 1000 μg of 2, 22.5 μg of 1 and 25 μg of 2, 22.5 μg of 1 and 50 μg of 2, 22.5 μg of 1 and 100 μg of 2, 22.5 μg of 1 and 200 μg of 2, 22.5 μg of 1 and 300 μg of 2, 22.5 μg of 1 and 400 μg of 2, 22.5 μg of 1 and 500 μg of 2, 22.5 μg of 1 and 600 μg of 2, 22.5 μg of 1 and 700 μg of 2, 22.5 μg of 1 and 800 μg of 2, 22.5 μg of 1 and 900 μg of 2, 22.5 μg of 1 and 1000 μg of 2, 25 μg of 1 and 25 μg of 2, 25 μg of 1 and 50 μg of 2, 25 μg of 1 and 100 μg of 2, 25 μg of 1 and 200 μg of 2, 25 μg of 1 and 300 μg of 2, 25 μg of 1 and 400 μg of 2, 25 μg of 1 and 500 μg of 2, 25 μg of 1 and 600 μg of 2, 25 μg of 1 and 700 μg of 2, 25 μg of 1 and 800 μg of 2, 25 μg of 1 and 900 μg of 2, 25 μg of 1 and 1000 μg of 2, 43.3 μg of 1 and 25 μg of 2, 45 μg of 1 and 50 μg of 2, 45 μg of 1 and 100 μg of 2, 45 μg of 1 and 200 μg of 2, 45 μg of 1 and 300 μg of 2, 45 μg of 1 and 400 μg of 2, 45 μg of 1 and 500 μg of 2, 45 μg of 1 and 600 μg of 2, 45 μg of 1 and 700 μg of 2, 45 μg of 1 and 800 μg of 2, 45 μg of 1 and 900 μg of 2, 45 μg of 1 and 1000 μg of 2, 50 μg of 1 and 25 μg of 2, 50 μg of 1 and 50 μg of 2, 50 μg of 1 and 100 μg of 2, 50 μg of 1 and 200 μg of 2, 50 μg of 1 and 300 μg of 2, 50 μg of 1 and 400 μg of 2, 50 μg of 1 and 500 μg of 2, 50 μg of 1 and 600 μg of 2, 50 μg of 1 and 700 μg of 2, 50 μg of 1 and 800 μg of 2, 50 μg of 1 and 900 μg of 2, 50 μg of 1 and 1000 μg of 2.

The active substance combinations of 1 and 2 according to the invention are preferably administered by inhalation. For this purpose, ingredients 1 and 2 have to be made available in forms suitable for inhalation. Inhalable preparations include inhalable powders, propellant-containing metering aerosols or propellant-free inhalable solutions. Inhalable powders according to the invention containing the combination of active substances 1 and 2 may consist of the active substances on their own or of a mixture of the active substances with physiologically acceptable excipients. Within the scope of the present invention, the term propellant-free inhalable solutions also includes concentrates or sterile inhalable solutions ready for use. The preparations according to the invention may contain the combination of active substances 1 and 2 either together in one formulation or in two separate formulations. These formulations which may be used within the scope of the present invention are described in more detail in the next part of the specification.

A) Inhalable Powder Containing the Combinations of Active Substances 1 and 2 According to the Invention The inhalable powders according to the invention may contain 1 and 2 either on their own or in admixture with suitable physiologically acceptable excipients.

If the active substances 1 and 2 are present in admixture with physiologically acceptable excipients, the following physiologically acceptable excipients may be used to prepare these inhalable powders according to the invention: monosaccharides (e.g. glucose or arabinose), disaccharides (e.g. lactose, saccharose, maltose), oligo- and polysaccharides (e.g. dextran), polyalcohols (e.g. sorbitol, mannitol, xylitol), salts (e.g. sodium chloride, calcium carbonate) or mixtures of these excipients with one another. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred.

Within the scope of the inhalable powders according to the invention the excipients have a maximum average particle size of up to 250 $\mu$m, preferably between 10 and 150 $\mu$m, most preferably between 15 and 80 $\mu$m. It may sometimes seem appropriate to add finer excipient fractions with an average particle size of 1 to 9 $\mu$m to the excipient mentioned above. These finer excipients are also selected from the group of possible excipients listed hereinbefore. Finally, in order to prepare the inhalable powders according to the invention, micronised active substance 1 and 2, preferably with an average particle size of 0.5 to 10 $\mu$m, more preferably from 1 to 6 $\mu$m, is added to the excipient mixture. Processes for producing the inhalable powders according to the invention by grinding and micronising and by finally mixing the ingredients together are known from the prior art. The inhalable powders according to the invention may be prepared and administered either in the form of a single powder mixture which contains both 1 and 2 or in the form of separate inhalable powders which contain only 1 and 2.

The inhalable powders according to the invention may be administered using inhalers known from the prior art. Inhalable powders according to the invention which contain a physiologically acceptable excipient in addition to 1 and 2 may be administered, for example, by means of inhalers which deliver a single dose from a supply using a measuring chamber as described in U.S. Pat. No. 4,570,630A, or by other means as described in DE 36 25 685 A. Preferably, the inhalable powders according to the invention which contain physiologically acceptable excipient in addition to 1 and 2 are packed into capsules (to produce so-called inhalettes) which are used in inhalers as described, for example, in WO 94/28958.

A particularly preferred inhaler for using the pharmaceutical combination according to the invention in inhalettes is shown in FIG. 1.

This inhaler (Handyhaler) for inhaling powdered pharmaceutical compositions from capsules is characterised by a housing 1 containing two windows 2, a deck 3 in which there are air inlet ports and which is provided with a screen 5 secured via a screen housing 4, an inhalation chamber 6 connected to the deck 3 on which there is a push button 8 provided with two sharpened pins 7 and movable counter to a spring 8, and a mouthpiece 12 which is connected to the housing 1, the deck 3 and a cover 11 via a spindle 10 to enable it to be flipped open or shut.

If the inhalable powders according to the invention are packed into capsules (inhalers) for the preferred use described above, the quantities packed into each capsule should be 1 to 30 mg, preferably 3 to 20 mg, more particularly 5 to 10 mg of inhalable powder per capsule. These capsules contain, according to the invention, either together or separately, the doses of 1' and 2 mentioned hereinbefore for each single dose.

B) Propellant Gas-driven Inhalation Aerosols Containing the Combinations of Active Substances 1 and 2

Inhalation aerosols containing propellant gas according to the invention may contain substances 1 and 2 dissolved in the propellant gas or in dispersed form. 1 and 2 may be present in separate formulations or in a single preparation, in which 1 and 2 are either both dissolved, both dispersed or only one component is dissolved and the other is dispersed. The propellant gases which may be used to prepare the inhalation aerosols according to the invention are known from the prior art. Suitable propellant gases are selected from among hydrocarbons such as n-propane, n-butane or isobutane and halohydrocarbons such as chlorinated and/or fluorinated derivatives of methane, ethane, propane, butane, cyclopropane or cyclobutane. The propellant gases mentioned above may be used on their own or in mixtures thereof. Particularly preferred propellant gases are halogenated alkane derivatives selected from TG11, TG12, TG134a and TG227. Of the halogenated hydrocarbons mentioned above, TG134a (1,1,1,2 -tetrafluoroethane) and TG227 (1,1,1,2,3,3,3 -heptafluoropropane) and mixtures thereof are preferred according to the invention.

The propellant-driven inhalation aerosols according to the invention may also contain other ingredients such as co-solvents, stabilisers, surfactants, antioxidants, lubricants and pH adjusters. All these ingredients are known in the art.

The inhalation aerosols containing propellant gas according to the invention may contain up to 5 wt.-% of active substance 1 and/or 2. Aerosols according to the invention contain, for example, 0.002 to 5 wt.-%, 0.01 to 3 wt.-%, 0.015 to 2 wt.-%, 0.1 to 2 wt.-%, 0.5 to 2 wt.-% or 0.5 to 1 wt.-% of active substance 1 and/or 2.

If the active substances 1 and/or 2 are present in dispersed form, the particles of active substance preferably have an average particle size of up to 10 $\mu$m, preferably from 0.1 to 5 $\mu$m, more preferably from 1 to 5 $\mu$m.

The propellant-driven inhalation aerosols according to the invention mentioned above may be administered using inhalers known in the art (MDIs=metered dose inhalers). Accordingly, in another aspect, the present invention relates to pharmaceutical compositions in the form of propellant-driven aerosols as hereinbefore described combined with one or more inhalers suitable for administering these aerosols. In addition, the present invention relates to inhalers which are characterised in that they contain the propellant gas-containing aerosols described above according to the invention. The present invention also relates to cartridges which are fitted with a suitable valve and can be used in a suitable inhaler and which contain one of the above-mentioned propellant gas-containing inhalation aerosols according to the invention. Suitable cartridges and methods of filling these cartridges with the inhalable aerosols containing propellant gas according to the invention are known from the prior art.

C) Propellant-free Inhalable Solutions or Suspensions Containing the Combinations of Active Substances 1 and 2 According to the Invention It is particularly preferred to use the active substance combination according to the invention in the form of propellant-free inhalable solutions and suspensions. The solvent used may be an aqueous or alcoholic, preferably an ethanolic solution. The solvent may be water on its own or a mixture of water and ethanol. The relative proportion of ethanol compared with water is not limited but the maximum is up to 70 percent by volume, more particularly up to 60 percent by volume and most preferably up to 30 percent by volume. The remainder of the volume is made up of water. The solutions or suspensions containing 1 and 2, separately or together, are adjusted to a pH of 2 to 7, preferably 2 to 5, using suitable acids. The pH may be adjusted using acids selected from inorganic or organic acids. Examples of suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with one of the active substances. Of the organic acids, ascorbic acid, fumaric acid and citric acid are preferred. If desired, mixtures of the above acids may be used, particularly in the case of acids which have other properties in addition to their acidifying qualities, e.g. as flavourings, antioxidants or complexing agents, such as citric acid or ascorbic acid, for example. According to the invention, it is particularly preferred to use hydrochloric acid to adjust the pH.

According to the invention, the addition of editic acid (EDTA) or one of the known salts thereof, sodium editate, as stabiliser or complexing agent is unnecessary in the present formulation. Other embodiments may contain this compound or these compounds. In a preferred embodiment the content based on sodium editate is less than 100 mg/100 ml, preferably less than 50 mg/100 ml, more preferably less than 20 mg/100 ml. Generally, inhalable solutions in which the content of sodium editate is from 0 to 10 mg/100 ml are preferred.

Co-solvents and/or other excipients may be added to the propellant-free inhalable solutions according to the invention. Preferred co-solvents are those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters. The terms excipients and additives in this context denote any pharmacologically acceptable substance which is not an active substance but which can be formulated with the active substance or substances in the pharmacologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilisers, complexing agents, antioxidants and/or preservatives which guarantee or prolong the shelf life of the finished pharmaceutical formulation, flavourings, vitamins and/or other additives known in the art. The additives also include pharmacologically acceptable salts such as sodium chloride as isotonic agents.

The preferred excipients include antioxidants such as ascorbic acid, for example, provided that it has not already been used to adjust the pH, vitamin A, vitamin E, tocopherols and similar vitamins and provitamins occurring in the human body.

Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art. The preservatives mentioned above are preferably present in concentrations of up to 50 mg/100 ml, more preferably between 5 and 20 mg/100 ml.

Preferred formulations contain, in addition to the solvent water and the combination of active substances 1 and 2, only benzalkonium chloride and sodium editate. In another preferred embodiment, no sodium editate is present.

The propellant-free inhalable solutions according to the invention are administered in particular using inhalers of the kind which are capable of nebulising a small amount of a liquid formulation in the therapeutic dose within a few seconds to produce an aerosol suitable for therapeutic inhalation. Within the scope of the present invention, preferred inhalers are those in which a quantity of less than 100 $\mu$L, preferably less than 50 $\mu$L, more preferably between 20 and 30 $\mu$L of active substance solution can be nebulised in preferably one spray action to form an aerosol with an average particle size of less than 20 $\mu$m, preferably less than 10 $\mu$m, in such a way that the inhalable part of the aerosol corresponds to the therapeutically effective quantity.

An apparatus of this kind for propellant-free delivery of a metered quantity of a liquid pharmaceutical composition for inhalation is described for example in International Patent Application WO 91/14468 and also in WO 97/12687 (cf. in particular FIGS. 6a and 6b). The nebulisers (devices) described therein are known by the name Respimat®.

This nebuliser (Respimat®) can advantageously be used to produce the inhalable aerosols according to the invention containing the combination of active substances 1 and 2. Because of its cylindrical shape and handy size of less than 9 to 15 cm long and 2 to 4 cm wide, this device can be carried at all times by the patient. The nebuliser sprays a defined volume of pharmaceutical formulation using high pressures through small nozzles so as to produce inhalable aerosols.

The preferred atomiser essentially consists of an upper housing part, a pump housing, a nozzle, a locking mechanism, a spring housing, a spring and a storage container, characterised by a pump housing which is secured in the upper housing part and which comprises at one end a nozzle body with the nozzle or nozzle arrangement, a hollow plunger with valve body, a power takeoff flange in which the hollow plunger is secured and which is located in the upper housing part, a locking mechanism situated in the upper housing part, a spring housing with the spring contained therein, which is rotatably mounted on the upper housing part by means of a rotary bearing, a lower housing part which is fitted onto the spring housing in the axial direction.

The hollow plunger with valve body corresponds to a device disclosed in WO 97/12687. It projects partially into the cylinder of the pump housing and is axially movable within the cylinder. Reference is made in particular to FIGS. 1 to 4, especially FIG. 3, and the relevant parts of the description. The hollow plunger with valve body exerts a pressure of 5 to 60 Mpa (about 50 to 600 bar), preferably 10 to 60 Mpa (about 100 to 600 bar) on the fluid, the measured amount of active substance solution, at its high pressure end at the moment when the spring is actuated. Volumes of 10 to 50 microliters are preferred, while volumes of 10 to 20 micrbliters are particularly preferred and a volume of 15 microliters per spray is most particularly preferred.

The valve body is preferably mounted at the end of the hollow plunger facing the valve body.

The nozzle in the nozzle body is preferably microstructured, i.e. produced by microtechnology. Microstructured valve bodies are disclosed for example in WO-94/07607; reference is hereby made to the contents of this specification, particularly FIG. 1 therein and the associated description.

The valve body consists for example of two sheets of glass and/or silicon firmly joined together, at least one of which has one or more microstructured channels which connect the nozzle inlet end to the nozzle outlet end. At the nozzle outlet end there is at least one round or non-round opening 2 to 10 microns deep and 5 to 15 microns wide, the depth preferably being 4.5 to 6.5 microns while the length is preferably 7 to 9 microns.

In the case of a plurality of nozzle openings, preferably two, the directions of spraying of the nozzles in the nozzle body may extend parallel to one another or may be inclined relative to one another in the direction of the nozzle opening. In a nozzle body with at least two nozzle openings at the outlet end the directions of spraying may be at an angle of 20 to 160° to one another, preferably 60 to 150°, most preferably 80 to 100°. The nozzle openings are preferably arranged at a spacing of 10 to 200 microns, more preferably at a spacing of 10 to 100 microns, most preferably 30 to 70 microns. Spacings of 50 microns are most preferred. The directions of spraying will therefore meet in the vicinity of the nozzle openings.

The liquid pharmaceutical preparation strikes the nozzle body with an entry pressure of up to 600 bar, preferably 200 to 300 bar, and is atomised into an inhalable aerosol through the nozzle openings. The preferred particle or droplet sizes of the aerosol are up to 20 microns, preferably 3 to 10 microns.

The locking mechanism contains a spring, preferably a cylindrical helical compression spring, as a store for the mechanical energy. The spring acts on the power takeoff flange as an actuating member the movement of which is determined by the position of a locking member. The travel of the power takeoff flange is precisely limited by an upper and lower stop. The spring is preferably biased, via a power step-up gear, e.g. a helical thrust gear, by an external torque which is produced when the upper housing part is rotated counter to the spring housing in the lower housing part. In this case, the upper housing part and the power takeoff flange have a single or multiple V-shaped gear.

The locking member with engaging locking surfaces is arranged in a ring around the power takeoff flange. It consists, for example, of a ring of plastic or metal which is inherently radially elastically deformable. The ring is arranged in a plane at right angles to the atomiser axis. After the biasing of the spring, the locking surfaces of the locking member move into the path of the power takeoff flange and prevent the spring from relaxing. The locking member is actuated by means of a button. The actuating button is connected or coupled to the locking member. In order to actuate the locking mechanism, the actuating button is moved parallel to the annular plane, preferably into the atomiser; this causes the deformable ring to deform in the annual plane. Details of the construction of the locking mechanism are given in WO 97/20590.

The lower housing part is pushed axially over the spring housing and covers the mounting, the drive of the spindle and the storage container for the fluid.

When the atomiser is actuated the upper housing part is rotated relative to the lower housing part, the lower housing part taking the spring housing with it. The spring is thereby compressed and biased by means of the helical thrust gear and the locking mechanism engages automatically. The angle of rotation is preferably a whole-number fraction of 360 degrees, e.g. 180 degrees. At the same time as the spring is biased, the power takeoff part in the upper housing part is moved along by a given distance, the hollow plunger is withdrawn inside the cylinder in the pump housing, as a result of which some of the fluid is sucked out of the storage container and into the high pressure chamber in front of the nozzle.

If desired, a number of exchangeable storage containers which contain the fluid to be atomised may be pushed into the atomiser one after another and used in succession. The storage container contains the aqueous aerosol preparation according to the invention.

The atomising process is initiated by pressing gently on the actuating button. As a result, the locking mechanism opens up the path for the power takeoff member. The biased spring pushes the plunger into the cylinder of the pump housing. The fluid leaves the nozzle of the atomiser in atomised form.

Further details of construction are disclosed in PCT Applications WO 97/12683 and WO 97/20590, to which reference is hereby made.

The components of the atomiser (nebuliser) are made of a material which is suitable for its purpose. The housing of the atomiser and—if its operation permits, other parts as well are preferably made of plastics, e.g. by injection moulding. For medicinal purposes, physiologically safe materials are used.

Figure 2A:
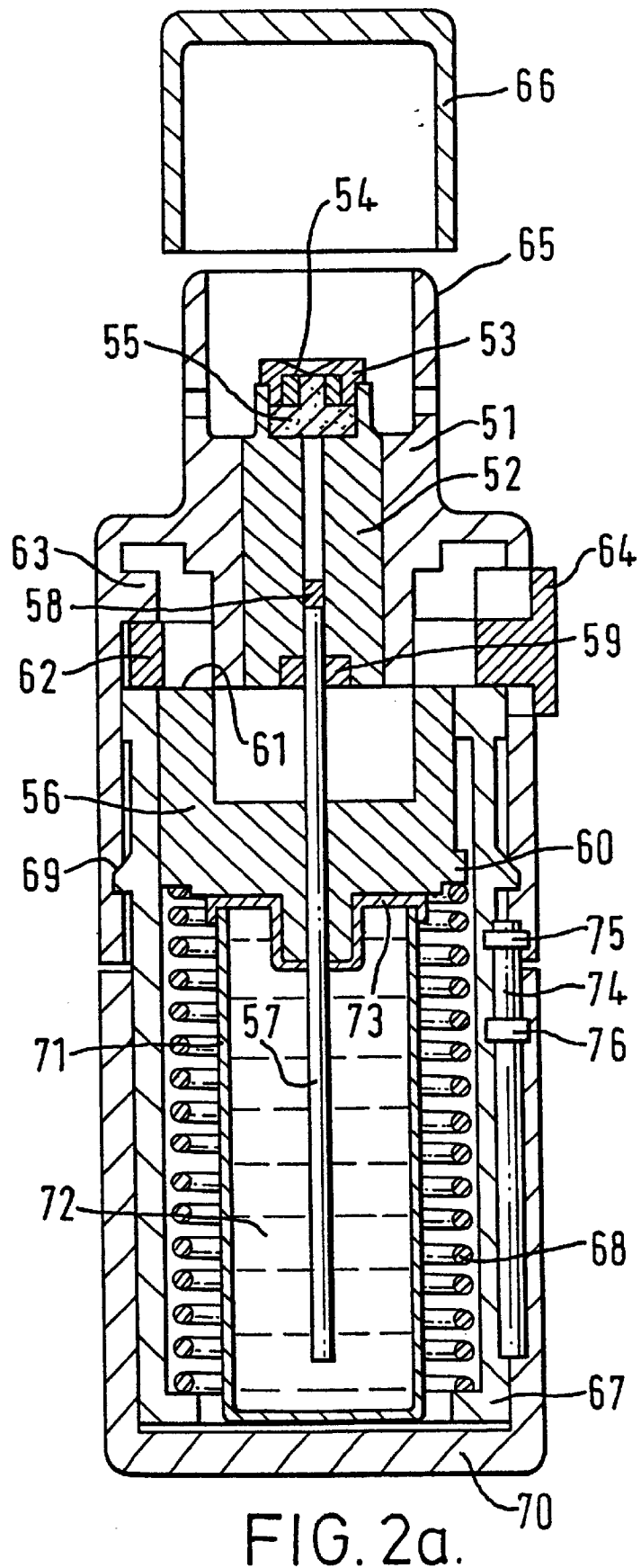

FIGS. 2a/b attached to this patent application, which are identical to FIGS. 6a/b of WO 97/12687, show the nebuliser (Respimat®) which can advantageously be used for inhaling the aqueous aerosol preparations according to the invention.

Figure 2B:
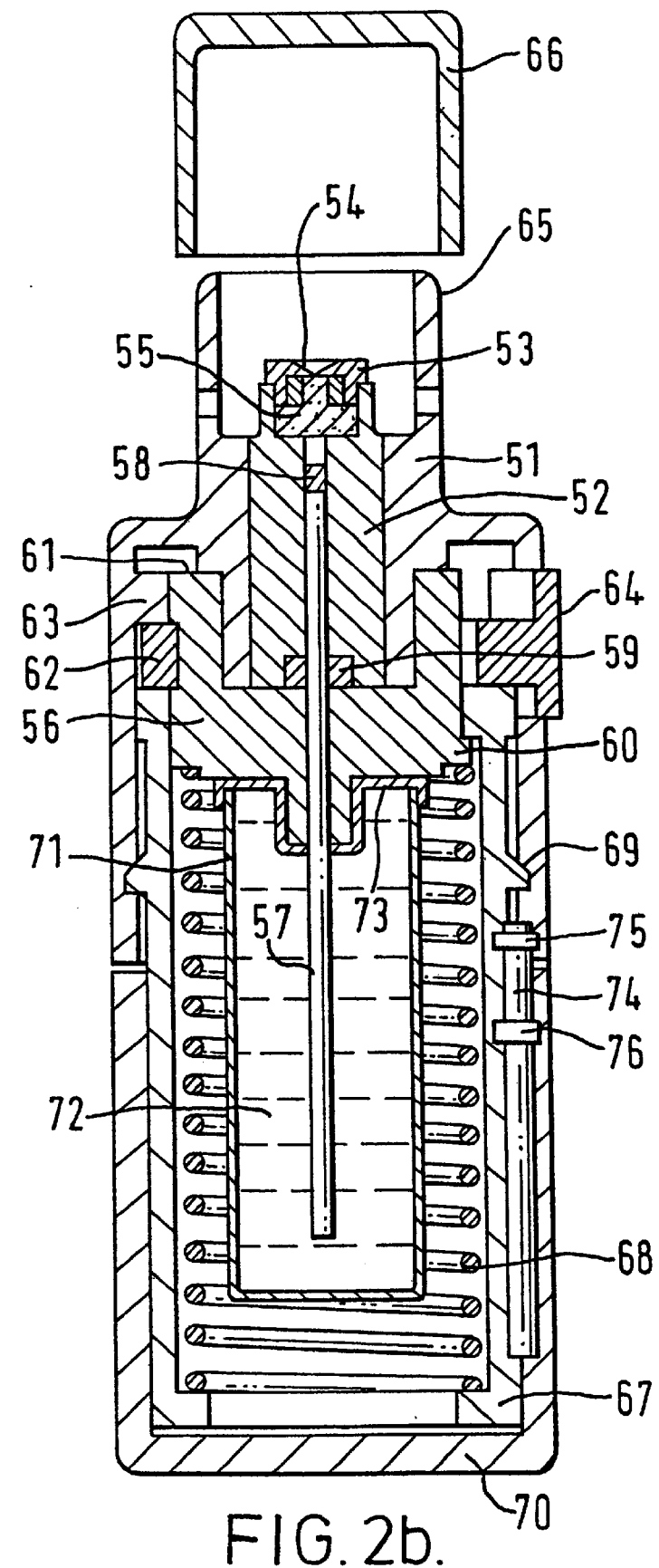

FIG. 2a shows a longitudinal section through the atomiser with the spring biased while FIG. 2b shows a longitudinal section through the atomiser with the spring relaxed.

The upper housing part (51) contains the pump housing (52) on the end of which is mounted the holder (53) for the atomiser nozzle. In the holder is the nozzle body (54) and a filter (55). The hollow plunger (57) fixed in the power takeoff flange (56) of the locking mechanism projects partially into the cylinder of the pump housing. At its end the hollow plunger carries the valve body (58). The hollow plunger is sealed off by means of the seal (59). Inside the upper housing part is the stop (60) on which the power takeoff flange abuts when the spring is relaxed. On the power takeoff flange is the stop (61) on which the power takeoff flange abuts when the spring is biased. After the biasing of the spring the locking member (62) moves between the stop (61) and a support (63) in the upper housing part. The actuating button (64) is connected to the locking member. The upper housing part ends in the mouthpiece (65) and is sealed off by means of the protective cover (66) which can be placed thereon.

The spring housing (67) with compression spring (68) is rotatably mounted on the upper housing part by means of the snap-in lugs (69) and rotary bearing. The lower housing part (70) is pushed over the spring housing. Inside the spring housing is the exchangeable storage container (71) for the fluid (72) which is to be atomised. The storage container is sealed off by the stopper (73) through which the hollow plunger projects into the storage container and is immersed at its end in the fluid (supply of active substance solution).

The spindle (74) for the mechanical counter is mounted in the covering of the spring housing. At the end of the spindle facing the upper housing part is the drive pinion (75). The slider (76) sits on the spindle.

The nebuliser described above is suitable for nebulising the aerosol preparations according to the invention to produce an aerosol suitable for inhalation.

If the formulation according to the invention is nebulised using the method described above (Respimat®) the quantity delivered should correspond to a defined quantity with a tolerance of not more than 25%, preferably 20% of this amount in at least 97%, preferably at least 98% of all operations of the inhaler (spray actuations). Preferably, between 5 and 30 mg of formulation, most preferably between 5 and 20 mg of formulation are delivered as a defined mass on each actuation.

However, the formulation according to the invention may also be nebulised by means of inhalers other than those described above, e.g. jet stream inhalers or other stationary nebulisers.

Accordingly, in a further aspect, the invention relates to pharmaceutical formulations in the form of propellant-free inhalable solutions or suspensions as described above combined with a device suitable for administering these formulations, preferably in conjunction with the Respimat®. Preferably, the invention relates to propellant-free inhalable solutions or suspensions characterised by the combination of active substances <u>1</u> and <u>2</u> according to the invention in conjunction with the device known by the name Respimat®. In addition, the present invention relates to the above-mentioned devices for inhalation, preferably the Respimat®, characterised in that they contain the propellant-free inhalable solutions or suspensions according to the invention as described hereinbefore.

The propellant-free inhalable solutions or suspensions according to the invention may take the form of concentrates or sterile inhalable solutions or suspensions ready for use, as well as the above-mentioned solutions and suspensions designed for use in a Respimat®. Formulations ready for use may be produced from the concentrates, for example, by the addition of isotonic saline solutions. Sterile formulations ready for use may be administered using energy-operated fixed or portable nebulisers which produce inhalable aerosols by means of ultrasound or compressed air by the Venturi principle or other principles.

Accordingly, in another aspect, the present invention relates to pharmaceutical compositions in the form of propellant-free inhalable solutions or suspensions as described hereinbefore which take the form of concentrates or sterile formulations ready for use, combined with a device suitable for administering these solutions, characterised in that the device is an energy-operated free-standing or portable nebuliser which produces inhalable aerosols by means of ultrasound or compressed air by the Venturi principle or other methods.

The Examples which follow serve to illustrate the present invention in more detail without restricting the scope of the invention to the following embodiments by way of example.

Starting Materials

Tiotropium Bromide

The tiotropium bromide used in the following formulations examples may be obtained as described in European Patent Application 418 716 A1.

In order to prepare the inhalable powders according to the invention, crystalline tiotropium bromide monohydrate may also be used. This crystalline tiotropium bromide monohydrate may be obtained by the method described below.

15.0 kg of tiotropium bromide are placed in 25.7 kg of water in a suitable reaction vessel. The mixture is heated to 80–90° C. and stirred at constant temperature until a clear solution is formed. Activated charcoal (0.8 kg) moistened with water is suspended in 4.4 kg of water, this mixture is added to the solution containing the tiotropium bromide and the resulting mixture is rinsed with 4.3 kg of water. The mixture thus obtained is stirred for at least 15 minutes at 80–90° C. and then filtered through a heated filter into an apparatus preheated to an external temperature of 70° C. The filter is rinsed with 8.6 kg of water. The contents of the apparatus are cooled at 3–5° C. for every 20 minutes to a temperature of 20–25° C. The apparatus is cooled further to 10–15° C. using cold water and crystallisation is completed by stirring for at least another hour. The crystals are isolated using a suction filter dryer, the crystal slurry isolated is washed with 9 liters of cold water (10–15° C.) and cold acetone (10–15° C). The crystals obtained are dried at 25° C. in a nitrogen current over a period of 2 hours. Yield: 13.4 kg of tiotropium bromide monohydrate (86% of theory).

The crystalline tiotropium bromide monohydrate thus obtained is micronised by known methods in order to prepare the active substance in the form of the average particle size corresponding to the specifications according to the invention.

In order to prepare the compounds <u>2</u> mentioned within the scope of the present invention and not known in the prior art:

N-[2-(3,5-bis-trifluoromethyl-phenyl)-ethyl]-2-{4-[(3-hydroxy-propyl)-methyl-amino]-piperidin-1-yl}-N-methyl-2-phenyl-acetamide a)

33 g of 1-benzyl-4-piperidone and 15 g of 3-aminopropanol are combined with a catalytic amount of p-toluenesulphonic acid in 300 ml of toluene and refluxed using the water separator until the calculated amount of water has been drawn off. Then the toluene is distilled off, the residue is dissolved in 250 ml of alcohol and cooled to about 5° C. A total of 6.6 g of sodium borohydride is added batchwise with stirring and the mixture is stirred for 30 hours at ambient temperature. It is combined with 50 ml of acetone, stirred for about half an hour and then the solvents are eliminated in vacuo. The residue is combined with 100 ml of water and extracted twice with 150 ml of methylene chloride. The combined organic phases are dried. The mixture is filtered, the solvent is eliminated in vacuo, the residue is taken up in 80 ml of alcohol, combined with 40 ml of 32% hydrochloric acid, diluted with acetone and stirred for about an hour. The crystals then precipitated are suction filtered and dried. 1-Benzyl-4-(3-hydroxypropylamino)-piperidine is obtained as the dihydrochloride.

b)

From 47.4 g of 1-benzyl-4-(3-hydroxypropylamino)-piperidine-dihydrochloride the base is liberated, combined with 63 ml of 85% formic acid and 22 ml of 37% formaldehyde solution and stirred for two hours at about 90–100° C. The mixture is left to cool, 37 ml of formic acid and 11 ml of formaldehyde solution are added and it is stirred for another hour at about 100–110° C. It is left to cool, combined with 150 ml of methanol, made alkaline with about 270 ml of 32% sodium hydroxide solution with cooling and stirred for about another 30 minutes at 40–50° C. and then the methanol is distilled off. The residue is extracted with twice 100 ml of methylene chloride, the combined methylene chloride phases are dried, filtered and freed from solvent in vacuo. The residue is taken up in 80 ml Ethanol, acidified with 34 ml of 32% hydrochloric acid, combined with 100 ml of acetone and stirred. As soon as crystals have been precipitated more acetone is added. The precipitate is suction filtered, washed with acetone and dried. 42.8 g of 1-benzyl-4-[-(3-hydroxypropyl)-methylamino]-piperidine-dihydrochloride are obtained in the form of a solid.

c)
42.8 g of 1-benzyl-4-[(3-hydroxypropyl)-methylamino]-piperidine-dihydrochloride are dissolved in 450 ml of methanol, combined with 5 g of 5% palladium-charcoal and hydrogenated at about 50° C. with hydrogen at 4–5 bar. The catalyst is filtered off, the methanol is distilled off and the residue is stirred in acetone. Ether is added, the mixture is left to stand for about two hours and then the crystals are suction filtered. 28.7 g of 4-[-(3-hydroxypropyl)-methylamino]-piperidine-dihydrochloride are obtained in the form of a solid.

d)
9 g of 4-[-(3-hydroxypropyl)-methylamino]-piperidine-dihydrochloride are dissolved together with 14.5 g of N-[2-(3,5-bis-trifluoromethyl-phenyl)-ethyl]-2-methanesulphonyloxy-N-methyl-2-phenyl-acetamide (prepared analogously to the method described in WO 99/62893) in 125 ml DMF, combined with 20.5 g of potassium carbonate and stirred for about four hours at 80–90° C. After cooling the mixture is poured onto ice, extracted twice with 150 ml of ethyl acetate, the combined organic phases are twice washed with water and dried. The desiccant is filtered off, the solvent is eliminated in vacuo and the residue is chromatographed with methylene chloride/methanol/conc. ammonia solution 95:5:0.5 over silica gel. The uniform fractions according to TLC are combined and freed from solvent in vacuo. The residue of 9.5 g is taken up in methanol and combined with 3.4 g of fumaric acid. Then the methanol is distilled off apart from a small residue, acetone is added and the resulting mixture is stirred for about 30 minutes. The crystals precipitated are suction filtered, washed with acetone and ether and dried. 9 g of N-2-N-[2-(3,5-bis-trifluoromethyl-phenyl)-ethyl]-2-{4-[(3-hydroxypropyl)-methyl-amino]-piperidin-1-yl}-N-methyl-2-phenyl-acetamide are obtained as the colourless sesquifumarate, m.p. 139–144° C.

$^1$H-NMR (250 MHz, CD$_3$OD) δ=7.85–7.26 (8H, m); 6.71 (3H, s); 4.50; 4.49 (1H, 2s); 3.67 (2H, t, J=6.0 Hz); 3.89–3.09 (7H, m); 3.21; 3.00 (4H, m);2.69; 2.94 (3H,); 2.77 (3H, s); 2.49–1.63 (6H, m); most of the signals are cleaved as a result of amide rotation.

N-[2-(3,5-bis-trifluoromethyl-phenyl)-ethyl]-2-[4-(2-hydroxy-1-hydroxymethyl-ethylamino)-piperidin-1-yl]-N-methyl-2-phenylacetamide a)
2.75 g of 2-aminopropan-1,3-diol and 5.9 g of 1-benzyl-4-piperidone are dissolved in 60 ml of methylene chloride and while cooling with ice a total of 9.9 g of sodium triacetoxyborohydride are added batchwise. The mixture is left to stand overnight at ambient temperature. 60 ml of methylene chloride and some water are added, then conc. hydrochloric acid is added while cooling with ice until an acid reaction is obtained. The mixture is stirred for about another 15 min. with cooling and then made clearly alkaline with 4 N sodium hydroxide solution. The aqueous phase is separated off, the organic phase is washed with a very little water, dried over sodium sulphate and freed from solvent in vacuo. 8 g of substance are obtained which are chromatographed with methylene chloride/methanol 8:2 over 150 g of silica gel. The uniform fractions according to TLC are combined and freed from solvent in vacuo. 7.3 g of 1-benzyl-4-(1,3-dihydroxyprop-2-ylamino)-piperidine are obtained.

b)
34.5 g of 1-benzyl-4-(1,3-dihydroxyprop-2-ylamino)-piperidine are dissolved in 400 ml of methanol, combined with 3.4 g of 20% palladium-charcoal and hydrogenated with hydrogen at 24–28° C. under 2.2 bar. Then the catalyst is filtered off and the solvent is eliminated in vacuo. 22.7 g of 4-(1,3-dihydroxyprop-2-ylamino)-piperidine are obtained as an oil, which is used for the next reaction without any further purification.

c)
9 g of 4-(1,3-dihydroxyprop-2-ylamino)-piperidine are reacted with 22.7 g of N-[2-(3,5-bis-trifluoromethyl-phenyl)-ethyl]-2-methanesulphonyloxy-N-methyl-2-phenyl-acetamide in 110 ml DMF with 7.2 ml of triethylamine as base analogously to Example 1, reaction time 5 h at 60–70° C. The crude product is chromatographed over silica gel with methylene chloride/methanol 9:1. The uniform fractions according to TLC are combined. The oily residue is taken up in ethyl acetate and a little water, the aqueous phase is made alkaline with conc. sodium hydroxide solution. The aqueous phase is separated off, the organic phase is dried and freed from solvent in vacuo. The residue is brought to crystallisation in acetone with methanesulphonic acid. 11 g of N-2-(3,5-N-[2-(3,5-bis-trifluoromethyl-phenyl)-ethyl]-2-[4-(2-hydroxy-1-hydroxymethyl-ethylamino)-piperidin-1-yl]-N-methyl-2-phenylacetamide are obtained as the colourless methanesulphonate.

$^1$H-NMR (250 MHz, CD$_3$OD) δ=7.95–7.31 (8H, m); 4.37; 4.31 ($^1$H, 2s); 3.77 (5H, m); 3.28 (1H, m); 3.05; 3.01 (4H, m); 2.74 (3H, s); 3.45–2.08 (4H, m); 2.07–1.52 (4H, m). Most of the signals are cleaved as a result of amide rotation.

N-[2-(3,5-bis-trifluoromethyl-phenyl)-ethyl]-2-[4-(cyclopropylmethyl-methyl-amino)-piperidin-1-yl]-N-methyl-2-phenyl-acetamide a)
19 g of 1-benzyl-4-piperidone are combined with 10 g Raney nickel (moistened by rinsing with a little methanol) and 40 g of methylamine in 150 ml of water and hydrogenated for eight hours at ambient temperature under 5 bars of hydrogen. Then the catalyst is filtered off, methanol and excess methylamine are eliminated in vacuo. The mixture is extracted with ethyl acetate, the organic phase is dried over sodium sulphate, filtered and evaporated down in vacuo. 19.2 g of a yellow oil are obtained, which is used for the next reaction without any further purification.

b)
18.9 g of 1-benzyl-4-methylaminopiperidine as the oil prepared according to a) are taken up in 250 ml of methanol and combined with 8.3 g of cyclopropanecarboxaldehyde and 11.3 g of sodium cyanoborohydride. The mixture is stirred for 5 hours at 40–50° C., then for about another 16 hours at ambient temperature. It is then acidified with 2 N hydrochloric acid, evaporated to dryness in vacuo and the residue is taken up in water. It is washed with ether, made alkaline with concentrated sodium hydroxide solution and extracted with ether/ethyl acetate. The organic extract is dried over sodium sulphate and freed from the solvents in vacuo. 22.7 g 1-benzyl-4-(cyclopropylmethyl-methyl-amino)-piperidine are obtained as a yellowish oil.

c)
21.5 g of the oil prepared according to b) are taken up in 230 ml of methanol, combined with 2.5 g of 10% palladium-charcoal and hydrogenated at 60° C. under 5 bars of hydrogen. After 3.5 hours the catalyst is renewed and the mixture is hydrogenated for a further five hours at 80° C. under 5 bars of hydrogen. Then the catalyst is filtered off and the solvent is eliminated in vacuo. 4-(Cyclopropylmethyl-methyl-amino)-piperidine is precipitated from the residue as the dihydrochloride with ethanolic hydrochloric acid. It is washed with ether, dried in vacuo and 12.5 g of colourless crystals are obtained.

d)

11.9 g of 4-(Cyclopropylmethyl-methyl-amino)-piperidine-dihydrochloride are taken up in 400 ml of acetone and combined with 21.7 g of N-[2-(3,5-bis-trifluoromethyl-phenyl)-ethyl]-2-methanesulphonyloxy-N-methyl-2-phenyl-acetamide and 21 ml of triethylamine. The mixture is refluxed for 16 hours, then the solvent is eliminated in vacuo and the residue is taken up in 10% sodium hydrogen carbonate solution. It is extracted with ether, the combined organic phases are dried over sodium sulphate and freed from solvent in vacuo. The residue is filtered with ethyl acetate/methanol/conc. ammonia solution 70:30:1 over silica gel, freed from the solvents in vacuo and brought to crystallisation in methanol with fumaric acid. The precipitate is suction filtered, washed with methanol and dried in vacuo. 9.3 g of N-[2-(3,5-bis-trifluoromethyl-phenyl)-ethyl]-2-[4-(cyclopropylmethyl-methyl-amino)-piperidin-1-yl]-N-methyl-2-phenyl-acetamide are obtained as the sesquifumarate.

$^1$H-NMR (250 MHz, CDCl$_3$) δ=7.71–7.14 (8H, m); 4.14 (1H, s); 3.81–2.46 (11H, m); 2.90; 2.82 (3H, 2s); 2.36 (3H, s); 2.23–1.48 (4H, m); 0.82 (1H, m); 0.48; 0.07 (4H, 2m). Most of the signals are cleaved as a result of amide rotation.

N-[2-(3,5-bis-trifluoromethyl-phenyl)-ethyl]-2-{4-[(2-hydroxy-ethyl)-(3-hydroxy-propyl)-amino]-piperidin-1-yl}-N-methyl-2-phenyl-acetamide a)

6 g of 2-hydroxyethyl-3-hydroxypropylamine and 18.9 g of 1-benzyl-4-piperidone are taken up in 250 ml methylene chloride and at 0° C. combined with 21.2 g of sodium triacetoxyborohydride. The mixture is stirred overnight at ambient temperature, then acidified with 2 N hydrochloric acid and made alkaline with concentrated sodium hydroxide solution. It is extracted with methylene chloride, the extract is dried over sodium sulphate and the solvent is eliminated in vacuo. The residue is chromatographed over silica gel with ethyl acetate/methanol/conc. ammonia solution 20:80:1. The uniform fractions according to TLC are combined and freed from solvent in vacuo. 2.3 g of 1-benzyl-4-[(2-hydroxy-ethyl)-(3-hydroxy-propyl)-amino]-piperidine are obtained as an oil.

b)

13.3 g of 1-benzyl-4-[(2-hydroxy-ethyl)-(3-hydroxy-propyl)-amino]-piperidine are combined with 1.5 g of 10% palladium-charcoal in 150 ml of methanol and hydrogenated at ambient temperature for 18 hours under 5 bars of hydrogen. The catalyst is renewed after 8 hours and 15 hours. Then the catalyst is filtered off and the filtrate is freed from solvent in vacuo. 4-[(2-Hydroxy-ethyl)-(3-hydroxy-propyl)-amino]-piperidine are obtained as an oil, which is used for the next reaction without any further purification.

c)

6.4 g of the oil of 4-[(2-hydroxy-ethyl)-(3-hydroxy-propyl)-amino]-piperidine prepared according to b) are taken up in 300 ml of acetone, combined with 13.8 g of N-[2-(3,5-bis-trifluoromethyl-phenyl)-ethyl]-2-methanesulphonyloxy-N-methyl-2-phenyl-acetamide and 33 ml of triethylamine and refluxed for 6 hours. The mixture is cooled, the solvent is eliminated in vacuo, the residue is stirred into 10% sodium hydrogen carbonate solution and extracted with ethyl acetate. The combined organic phases are dried over sodium sulphate, the solvent is eliminated in vacuo and the residue is chromatographed over silica gel with ethyl acetate/methanol/conc. ammonia solution 20:80:1. The uniform fractions according to TLC are combined and freed from the solvents in vacuo. 8.4 g of N-[2-(3,5-bis-trifluoromethyl-phenyl)-ethyl]-2-{4-[(2-hydroxy-ethyl)-(3-hydroxy-propyl)-amino]-piperidin-1-yl}-N-methyl-2-phenyl-acetamide are obtained as a yellowish-brown oil.

$^1$H-NMR (250 MHz, CDCl$_3$) δ=7.78–7.24 (8H, m); 4.24 (1H, s); 3.78(2H, m); 3.61 (2H, m); 3.64 (1H, m); 2.98; 2.87 (3H, 2s); 2.93 (4H, m); 2.74; 2.65 (4H, 2m); 2.88–1.77 (4H, m); 1.67 (2H, m); 1.76–1.45 (4H, m). Most of the signals are cleaved as a result of amide rotation.

(S)-N-[2-(3,5-bis-trifluoromethyl-phenyl)-ethyl]-2-{4-[cyclopropylmethyl-(3-hydroxy-propyl)-amino]-piperidin-1-yl}-N-methyl-2-phenyl-acetamide a)

16.5 g of 3-aminopropanol and 41.7 g of 1-benzyl-4-piperidone are dissolved in 350 ml methylene chloride and at about 10° C. 56 g of sodium triacetoxy-borohydride are slowly added. The mixture is stirred overnight at ambient temperature, then acidified with dilute hydrochloric acid with cooling and subsequently made alkaline with conc. sodium hydroxide solution. The organic phase is separated off, the aqueous phase is washed once again with 150 ml of methylene chloride. The combined organic phases are dried over sodium sulphate and freed from solvent in vacuo. 32 g 1-benzyl-4-(3-hydroxy-propylamino)-piperidine are obtained as a yellow oil which is used in the next reaction step without any further purification.

b)

13.4 g of 1-benzyl-4-(3-hydroxy-propylamino)-piperidine from the previous reaction are dissolved together with 3.8 g of cyclopropanecarboxaldehyde in 250 ml of methanol and at 0° C. combined with 5.1 g of sodium cyanoborohydride. The mixture is stirred overnight at ambient temperature, then acidified with dilute hydrochloric acid with cooling and evaporated down in vacuo. The mixture is then made alkaline with conc. sodium hydroxide solution and extracted three times with 40 ml of methylene chloride. The combined organic phases are dried over sodium sulphate, filtered and freed from solvent in vacuo. The residue is filtered over silica gel with ethyl acetate/methanol/conc. ammonia solution 20:80:1. After the solvent has been eliminated 10.2 g of 1-benzyl-4-[cyclopropylmethyl-(3-hydroxy-propyl)-amino]-piperidine are obtained as a yellow oil.

c)

10.2 g of 1-benzyl-4-[cyclopropylmethyl-(3-hydroxy-propyl)-amino]-piperidine are combined with 2 g of 20% palladium-charcoal in 100 ml of methanol and hydrogenated at 60° C. for 4 h under 5 bars of hydrogen. The catalyst is separated off, the solvent is eliminated in vacuo and 7.3 g of 4-[cyclopropylmethyl-(3-hydroxy-propyl)-amino]-piperidine are obtained as a yellow oil.

d)

4.7 g of 4-[cyclopropylmethyl-(3-hydroxy-propyl)-amino]-piperidine are stirred together with 9.6 g of (R)-N-[2-(3,5-bis-trifluoromethyl-phenyl)-ethyl]-2-methanesulphonyloxy-N-methyl-2-phenyl-acetamide (prepared from D-(−)-mandelic acid) and 3.4 ml of triethylamine in 200 ml of acetone for four hours at 65° C. The mixture is evaporated down in vacuo, combined with 100 ml of saturated sodium hydrogen carbonate solution and extracted with ethyl acetate. The combined organic fractions are dried over sodium sulphate and freed from solvent in vacuo. The residue is chromatographed with methylene chloride/methanol 1:1 over silica gel. The uniform fractions according to TLC are collected and the solvents are eliminated in vacuo. 5.5 g of (S)-N-[2-(3,5-bis-trifluoromethyl-phenyl)-ethyl]-2-{4-[cyclopropylmethyl-(3-hydroxy-propyl)-amino]-piperidin-1-yl}-N-methyl-2-phenyl-acetamide are obtained as a yellowish-brown oil, $[\alpha]_D^{20}$=+29.6°

$^1$H-NMR (250 MHz, CDCl$_3$) δ=7.78–7.26 (8H, m), 4.24 (1H, s), 3.78 (2H, m); 3,63 (2H, m); 3.50 (1H, m); 2.96; 2.88 (3H, 2s); 2.93 (4H, m); 2.88–1.77 (5H, m); 2.37 (2H, d, J=6.0 Hz); 1.79–1.45 (6H, m); 0.87 (1H, m); 0.52; 0.12 (4H, 2m). Most of the signals are cleaved as a result of amide rotation.

Examples of Formulations

A) Inhalable Powders

| Ingredients | μg per capsule |
|---|---|
| 1) Tiotropium bromide | 10.8 |
| NK$_1$-receptor antagonist | 27.9 |
| Lactose | 4961.3 |
| Total | 5000 |
| 2) Tiotropium bromide | 21.7 |
| NK$_1$-receptor antagonist | 55.9 |
| Lactose | 4922.4 |
| Total | 5000 |
| 3) Tiotropium bromide × H$_2$O | 22.5 |
| NK$_1$-receptor antagonist | 55.9 |
| Lactose | 4921.6 |
| Total | 5000 |
| 4) Tiotropium bromide | 21.7 |
| NK$_1$-receptor antagonist | 55.9 |
| Lactose | 4922.4 |
| Total | 5000 |

B) Propellant Gas-containing Aerosols for Inhalation

| Ingredients | wt - % |
|---|---|
| 1) Suspension aerosol: | |
| Tiotropium bromide | 0.015 |
| NK$_1$-receptor antagonist | 0.066 |
| Soya lecithin | 0.2 |
| TG 11:TG12 = 2:3 | ad 100 |
| 2) Suspension aerosol: | |
| Tiotropium bromide | 0.029 |
| NK$_1$-receptor antagonist | 0.033 |
| absolute ethanol | 0.5 |
| isopropyl myristate | 0.1 |
| TG 227 | ad 100 |
| 3) Suspension aerosol: | |
| Tiotropium bromide | 0.029 |
| NK$_1$-receptor antagonist | 0.033 |
| absolute ethanol | 0.5 |
| isopropyl myristate | 0.1 |
| TG 227 | ad 100 |
| 4) Suspension aerosol: | |
| Tiotropium bromide | 0.029 |
| NK$_1$-receptor antagonist | 0.033 |
| absolute ethanol | 0.5 |
| isopropyl myristate | 0.1 |
| TG 227 | ad 100 |

What is claimed is:

1. An inhalation aerosol pharmaceutical formulation which comprises as an active substance a salt of tiotropium combined with a second active substance which is one or more NK$_1$-receptor antagonists, in a propellant gas selected from among hydrocarbons such as n-propane, n-butane or isobutane and halohydrocarbons such as fluorinated derivatives of methane, ethane, propane, butane, cyclopropane or cyclobutane or in mixtures thereof, wherein the active substances may be formulated together and combined with the propellant gas or the active substances may be separately formulated and then the separate formulations combined with the propellant gas.

2. The inhalation aerosol formulation as recited in claim 1 wherein the propellant gas is selected from TG134a (1,1,1,2-tetrafluoroethane) and TG227 (1,1,1,2,3,3,3-heptafluoropropane) and mixtures thereof.

3. The inhalation aerosol formulation as recited in claim 1 wherein the salt of tiotropium is the chloride, bromide, iodide, methane sulphonate or paratoluene sulphonate salt.

4. The inhalation aerosol formulation as recited in claim 3 wherein the salt of tiotropium is the bromide salt.

5. The inhalation aerosol formulation as recited in claim 1 wherein the NK$_1$-receptor antagonist is selected from among BIIF 1149, CP-122721, FK-888, NKP 608C, NKP 608A, CGP 60829, SR 48968(Saredutant), SR 140333 (Nolpitantium besilate/chloride), LY 303 870 (Lanepitant), MEN-11420 (Nepadutant), SB 223412, MDL-105172A, MDL-103896, MEN-11149, MEN-11467, DNK 333A, SR-144190, YM-49244, YM-44778, ZM-274773, MEN-10930, S-19752, Neuronorm, YM-35375, DA-5018, MK-869, L-754030, CJ-11974, L-758298, DNK-33A, 6b-I, CJ-11974, TAK-637, GR 205171, N-[2-(3,5-bis-trifluoromethyl-phenyl)-ethyl]-2-{4-[(3-hydroxy-propyl)-methyl-amino]-piperidin-1-yl}-N-methyl-2-phenyl-acetamide, N-[2-(3,5-bis-trifluoromethyl-phenyl)-ethyl]-2-[4-(2-hydroxy-1-hydroxymethyl-ethylamino)-piperidin-1-yl]-N-methyl-2-phenylacetamide, BIIM1310 N-[2-(3,5-bis-trifluoromethyl-phenyl)-ethyl]-2-[4-(cyclopropylmethyl-methyl-amino)-piperidin-1-yl]-N-methyl-2-phenyl-acetamide, N-[2-(3,5-bis-trifluoromethyl-phenyl)-ethyl]-2-{4-[(2-hydroxy-ethyl)-(3-hydroxy-propyl)-amino]-piperidin-1-yl}-N-methyl-2-phenyl-acetamide, N-[2-(3,5-bis-trifluoromethyl-phenyl)-ethyl]-2-{4-[cyclopropylmethyl-(3-hydroxy-propyl)-amino]-piperidin-1-yl}-N-methyl-2-phenyl-acetamide and the arylglycinamide derivatives of general formula 3

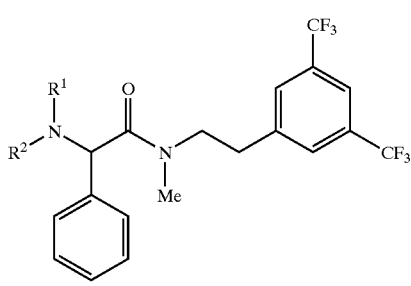

wherein

R$^1$ and R$^2$ together with the N to which they are bound form a ring of formula

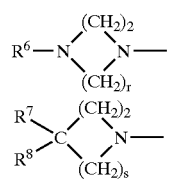

wherein r and s are 2 or 3;

R$^6$ denotes H, —C$_1$–C$_5$-alkyl, C$_3$–C$_5$-alkenyl, propynyl, hydroxy(C$_2$–C$_4$)alkyl, methoxy(C$_2$–C$_4$)alkyl, di(C$_1$–C$_3$)alkylamino(C$_2$–C$_4$)alkyl, amino (C$_2$–C$_4$)alkyl, amino, di(C$_1$–C$_3$)alkylamino, monofluoro to perfluoro(C$_1$–C$_2$)alkyl, N-methylpiperidinyl, pyridyl, pyrimidinyl, pyrazinyl or pyridazinyl, R$^7$ has one of the meanings (a) to (d), (a) hydroxy (b) 4-piperidinopiperidyl, (c)

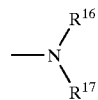

wherein R$^{16}$ and R$^{17}$ independently of each other denote H, (C$_1$–C$_4$)alkyl, (C$_3$–C$_6$)cycloalkyl, hydroxy(C$_2$–C$_4$)alkyl, dihydroxy(C$_2$–C$_4$)alkyl, (C$_1$–C$_3$)alkoxy(C$_2$–C$_4$)alkyl, phenyl(C$_1$–C$_4$)alkyl or di(C$_1$–C$_3$)alkylamino(C$_2$–C$_4$)alkyl, R$^8$ denotes H, optionally in the form of the enantiomers and mixtures of enantiomers thereof, optionally in the form of the racemates thereof.

6. The inhalation aerosol formulation as recited in claim 5 wherein the NK$_1$-receptor antagonist is selected from BIIF 1149,CP-122721, CGP 60829, MK-869, CJ-11974, GR 205171, N-[2-(3,5-bis-trifluoromethyl-phenyl)-ethyl]-2-{4-[(3-hydroxy-propyl)-methyl-amino]-piperidin-1-yl}-N-methyl-2-phenyl-acetamide, N-[2-(3,5-bis-trifluoromethyl-phenyl)-ethyl]-2-[4-(2-hydroxy-1-hydroxymethyl-ethylamino)-piperidin-1-yl]-N-methyl-2-phenylacetamide, BIIM1310 N-[2-(3,5-bis-trifluoromethyl-phenyl)-ethyl]-2-[4-(cyclopropylmethyl-methyl-amino)-piperidin-1-yl]-N-methyl-2-phenyl-acetamide, N-[2-(3,5-bis-trifluoromethyl-phenyl)-ethyl]-2-{4-[(2-hydroxy-ethyl)-(3-hydroxy-propyl)-amino]-piperidin-1-yl}-N-methyl-2-phenyl-acetamide, N-[2-(3,5-bis-trifluoromethyl-phenyl)-ethyl]-2-{4-2-phenyl-acetamide and the arylglycinamide derivatives of general formula 3, wherein R$^1$ and R$^2$ together with the N to which they are bound form a ring of formula

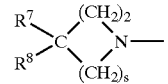

wherein s is 2 or 3;

R$^7$ denotes a group

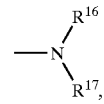

wherein R$^{16}$ and R$^{17}$ independently of each other denote H, (C$_1$–C$_4$)alkyl, (C$_3$–C$_6$)cycloalkyl, hydroxy(C$_2$–C$_4$)alkyl, dihydroxy(C$_2$–C$_4$)alkyl, (C$_1$–C$_3$)alkoxy(C$_2$–C$_4$)alkyl, phenyl(C$_1$–C$_4$)alkyl or di(C$_1$–C$_3$)alkylamino(C$_2$–C$_4$)alkyl, R$^8$ denotes H, optionally in the form of the enantiomers and mixtures of enantiomers thereof and optionally in the form of the racemates thereof.

7. The inhalation aerosol formulation as recited in claim 6 wherein the NK$_1$-receptor antagonist is selected from (S)-N-[2-(3,5-bis-trifluoromethyl-phenyl)-ethyl]-2-[4-(2-hydroxy-1-hydroxymethyl-ethylamino)-piperidin-1-yl]-N-methyl-2-phenylacetamide or an acid addition salt thereof.

8. The inhalation aerosol formulation as recited in claim 1 wherein the weight ratio of the tiotropium salt to the NK$_1$-receptor antagonist is about 1:300 to about 50:1.

9. The inhalation aerosol formulation in claim 8 wherein the weight ratio of the tiotropium salt to the NK$_1$-receptor antagonist is about 1:250 to about 40:1.

10. A method for treatment of asthma in a warm-blooded animal which comprises administering a therapeutically effective amount of an inhalation aerosol formulation as recited in claim 1.

11. A method for treatment of chronic obstructive pulmonary disease in a warm-blooded animal which comprises administering a therapeutically effective amount of an inhalation aerosol formulation as recited in claim 1.

12. The method for treatment of chronic obstructive pulmonary disease in a warm-blooded animal as recited in claim 11 wherein the tiotropium salt and the NK$_1$-receptor antagonist are present in separate formulations.

\* \* \* \* \*